United States Patent [19]

Rothfuss

[11] 4,319,576

[45] Mar. 16, 1982

[54] INTRALUMENAL ANASTOMOSIS SURGICAL STAPLING INSTRUMENT

[75] Inventor: Robert G. Rothfuss, Bellevue, Ky.

[73] Assignee: Senco Products, Inc., Cincinnati, Ohio

[21] Appl. No.: 124,954

[22] Filed: Feb. 26, 1980

[51] Int. Cl.³ .................. A61B 17/04; A61B 17/32
[52] U.S. Cl. .................................. 128/305; 227/19; 128/334 R
[58] Field of Search .............. 128/334, 334 C, 305, 128/335; 227/19, 76

[56] References Cited

U.S. PATENT DOCUMENTS

| | | | |
|---|---|---|---|
| 3,193,165 | 7/1965 | Akhalaya et al. | 227/19 |
| 3,490,675 | 1/1970 | Green et al. | 227/19 |
| 3,552,626 | 4/1968 | Astavfiev et al. | 227/19 X |
| 3,593,903 | 7/1971 | Astavfiev et al. | 227/19 X |
| 3,638,652 | 2/1972 | Kelly | 227/19 X |
| 3,692,224 | 9/1972 | Astavfiev et al. | 227/19 |
| 3,822,818 | 7/1974 | Strekopytov | 227/19 X |
| 3,836,061 | 9/1974 | Grunwald | 227/19 X |
| 4,047,654 | 9/1977 | Alvarado | 227/19 |
| 4,198,982 | 4/1980 | Fortner | 227/19 X |
| 4,207,898 | 6/1980 | Becht | 128/334 X |

Primary Examiner—Stephen C. Pellegrino
Attorney, Agent, or Firm—Frost & Jacobs

[57] ABSTRACT

A disposable surgical stapling instrument for the joining together of tubular body organs such as the organs of the alimentary canal. The instrument comprises an elongated body having a tubular housing portion and a coaxial cylindrical handle portion. The tubular housing portion supports at its free end a coaxial cylindrical casing containing at least one annular array of surgical staples. An adjusting rod is coaxially and non-rotatively mounted within the instrument body and has a first end extending beyond the staple-containing casing. An anvil, of improved configuration for easier removal from the anastomotic site, is removably mounted by means of an anvil nut on the first end of the adjusting rod facing the staple-containing casing. By means of an adjustment knob at the free end of the instrument body handle portion, the anvil and the adjusting rod are shiftable axially of the instrument body between a position wherein the anvil is adjacent the staple-containing casing and a position wherein the anvil is spaced from the staple-containing casing. The anvil has a plurality of anvil pockets formed therein to clinch the staples over a range of distances between the anvil and the staple casing constituting a working gap. The adjustment rod has a second end mounting an indicator cooperating with the adjustment knob to give both visual and tactile indications that the anvil is spaced from the staple casing within the operating gap. A ring scale is mounted on the adjusting knob enabling accurate setting of the distance between the anvil and the staple casing, within the working gap, according to the thickness of the tissue of the tubular body organs being joined. The instrument is also provided with a lever actuated staple driver and scalpel assembly and a slide safety lockout to prevent undesired actuation of the lever.

29 Claims, 13 Drawing Figures

INTRALUMENAL ANASTOMOSIS SURGICAL STAPLING INSTRUMENT

TECHNICAL FIELD

The invention relates to an intralumenal anastomosis surgical stapling instrument and more particularly to such an instrument which may readily be made in a single-use, disposable form and which is provided with improved operating gap setting and indicating means and an anvil configured both to properly clinch the staples over the full range of the operating gap and for easier removal of the tool from the joined tubular body organs.

BACKGROUND ART

Within the last decade there has been an ever increasing use of surgical staples, in lieu of conventional sutures, in many internal organ and intestinal procedures from the esophagus to the rectum. U.S. Pat. Nos. 3,193,165; 3,338,847; 3,552,626, 3,593,903 and 3,638,652. together with copending application Ser. No. 890,262, filed Mar. 27, 1978 in the name of Carl T. Becht and entitled INTRALUMENAL ANASTOMOSIS SURGICAL STAPLING INSTRUMENT, teach exemplary types of surgical stapling instruments devised by prior art workers for such procedures. The use of surgical staples and such surgical stapling instruments has made many difficult procedures much simpler. Of even greater importance, however, is the fact that the use of surgical staples significantly reduces the time required for such procedures and therefore reduces the length of time for which the patient must be maintained under anesthetic.

U.S. Pat. Nos. 3,193,165 and 3,388,847 are exemplary of permanent-type, reusable instruments requiring that the staples be hand-loaded into a single ring cartridge. Instruments of this type have several disadvantages. In general, they are complex in structure, expensive to manufacture, bulky and heavy. They must be constantly maintained; disassembled and cleaned after each use; and sterilized for each procedure. Staples must be individually hand-loaded into the cartridge for each procedure. The instrument scalpel must be sharpened periodically and special tools are frequently required for assembly, disassembly, maintenance and replacement of parts.

It is well known that the tubular structures constituting the human alimentary canal, i.e. the esaphogus, small and large intestines, are of varying diameters and wall thicknesses even within the same patient. In order to place a circular anastomosis in the tubular structures of the alimentary canal, instruments of the type described must be introduced into the inner spaced of the organ being sutured. The diameter of the staple containing portion of the instrument must correspond to the internal diameter of the organ being stapled.

The above noted U.S. Pat. No. 3,552,626 teaches interchangeable staple carrying heads of different diameters. Such an instrument, however, not only suffers from those disadvantages mentioned above, but in addition, the interchangeable heads are difficult to install and remove. The minimum size of such heads is limited because of the bulky fittings required for their joinder to the instrument. Furthermore, the instrument is provided with a knurled nose nut which can damage the inside of the intestine during removal of the instrument. The instrument of the above noted copending application can be made wholly disposable or can be a reusable instrument provided with a disposable staple cartridge. As a reusable instrument it would suffer from the drawbacks noted above.

Along with the advantages of the use of surgical staples and surgical stapling instruments, there are certain inherent dangers. First of all, it is necessary to select the proper staple size for the thickness of tissue to be joined. Secondly, even if the proper staple size is selected, the staples must not be formed too tightly or too loosely. If the staples are formed too tightly the blood supply needed for the healing process is cut off and the tissue becomes necrotic. If the staples are formed too loosely, then hemorrhaging and/or leakage can occur. Thus, both too tightly and too loosely formed staples can cause serious problems and complications.

The present invention is directed to an intralumenal anastomosis surgical stapling instrument of extremely simple design. While the instrument may be manufactured in the form of a permanent, reusable instrument, it is particularly adapted to manufacture as a single-use, disposable surgical stapling instrument. The instrument is capable of placing an "end-to-end", "end-to-side", "side-to-side" and "side-to-end" anastomosis. Since the instrument lends itself well to manufacture as a single-use, disposable instrument, it can readily be made in one or more lengths and with staple-containing casings of different diameters to cover most of the internal diameters encountered in the human alimentary canal.

The instrument of the present invention is light weight and easy to manipulate. While the staple-containing casing can mount a single annular array of staples, it preferably contains two staggered annular arrays of staples in concentric pattern eliminating the necessity for over-suturing to stop leakage and bleeding.

The instrument of the present invention is provided with improved gap setting means including means for giving both a visual and a tactile indication that the space between the anvil and the staple-containing casing is within the "working gap" of the instrument and calibrated adjustable vernier means for setting the actual gap, within the "working gap", at a distance appropriate for the thickness of tissues being joined. To this end, the surgical stapling instrument may be used in conjunction with a tissue thickness measuring device of the type, for example, taught in copending application Ser. No. 06/124,955, filed Feb. 26, 1980, in the names of Robert G. Rothfuss and Edwin L. Stith, Jr., and entitled SURGICAL TISSUE THICKNESS MEASURING INSTRUMENT.

The instrument may be provided with a slide safety lockout to prevent accidental ejection of the staples. The instrument may further be vented to equalize pressure on either side of an anastomosis, as will be described hereinafter.

Finally, prior art instruments of the type described have been characterized by the fact that they are difficult to remove from the anastomotic site after the staples are crimped and the tissue is joined. The instrument of the present invention is provided with an improved anvil of unique profile for easy removal of the instrument from the anastomotic site.

Heretofore surgical stapling instruments have been devised with anvil means configured to form the surgical staples into a B-shaped configuration. This is taught, for example, in U.S. Pat. Nos. 3,490,675 and 3,494,533.

The anvil of the present invention is provided with anvil pockets so configured as to adequately crimp the surgical staples into a B-shape throughout the range of the "working gap" without requiring the use of staples of different leg lengths.

DISCLOSURE OF THE INVENTION

According to the invention there is provided a disposable surgical stapling instrument for the joining together of tubular body organs such as the organs of the alimentary canal. The instrument comprises an elongated body in two halves permanently joined together and having a tubular housing portion and a coaxial cylindrical handle portion of larger diameter. The tubular housing portion supports at its free end a coaxial, cylindrical casing containing at least one annular array of surgical staples.

An adjusting rod is coaxially and non-rotatively mounted within the instrument body and has a first end extending beyond the staple containing casing. An anvil is removably mounted by means of an anvil nut on the first end of the adjusting rod, facing the staple containing casing. The anvil presents a flat annular surface toward the staple containing casing and its peripheral portion comprises a thin flange tapering forwardly and inwardly. By means of an adjustment nut at the free end of the instrument body handle portion, the anvil and the adjusting rod are shiftable axially of the instrument body between a position wherein the anvil is adjacent the staple-containing casing and a position wherein the anvil is spaced from the staple-containing casing. The anvil has a plurality of anvil pockets formed on its flat annular surface to clinch the staples over a range of distances between the anvil and the staple-containing casing constituting the "operating gap" of the instrument.

The adjustment rod has a second end mounting an indicator cooperating with the adjustment knob to give both visual and tactile indications that the anvil is spaced from the staple casing by a distance falling within the operating gap. A ring scale is mounted on the adjusting knob enabling accurate setting of the distances between the anvil and the staple-containing casing within the operating gap according to the thickness of the tissue of the tubular body organs being joined.

The instrument is also provided with a lever actuated staple driver and scalpel assembly for driving the staples through the tissue being joined and against the anvil and for removing excess tissue. The instrument may further be provided with a slide safety lockout, locking the lever in its unactuated position.

BEST MODE OF CARRYING OUT THE INVENTION

Figure 1:
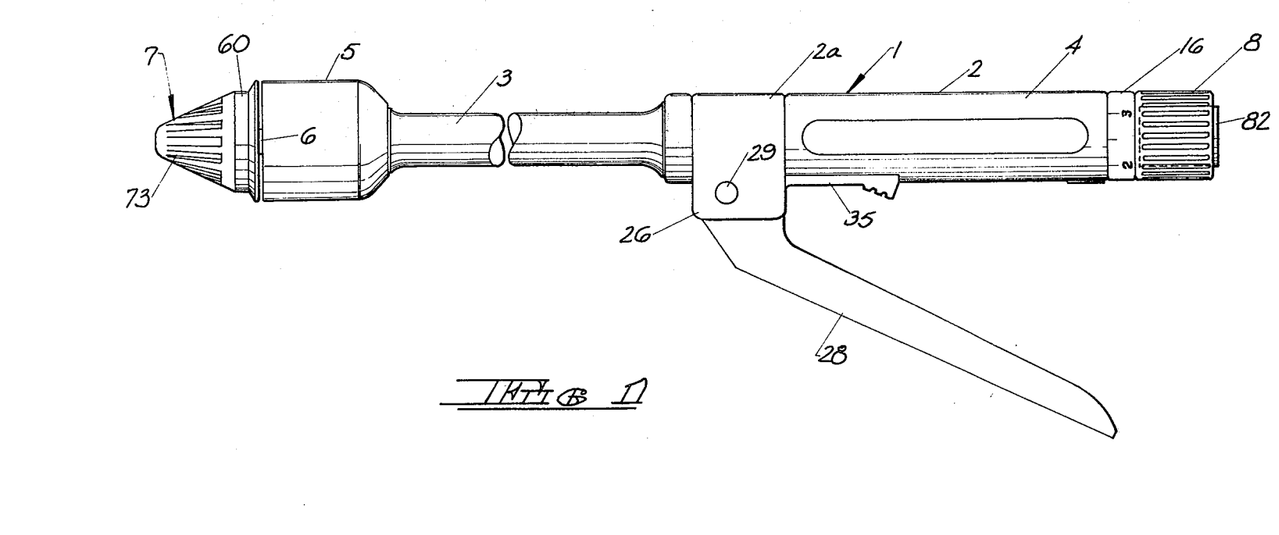
FIG. 1 is a fragmentary side elevational view of the intralumenal anastomosis surgical stapling instrument of the present invention.
Figure 2:
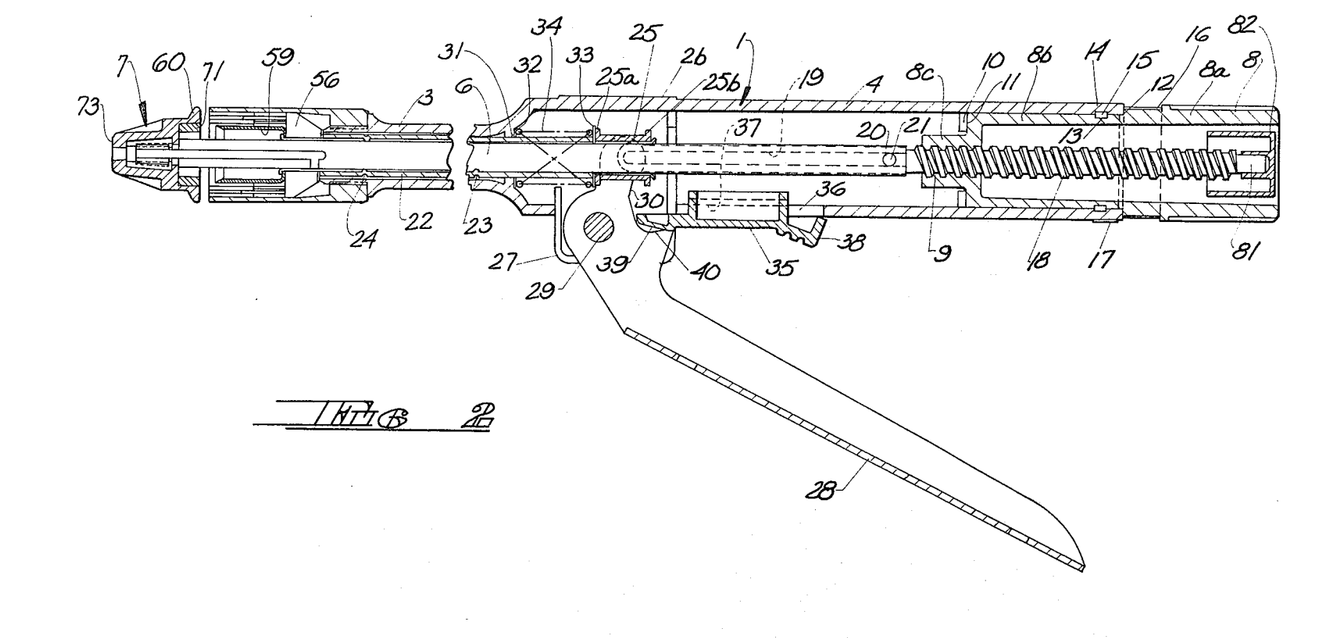
FIG. 2 is a fragmentary longitudinal cross sectional view of the instrument of FIG. 1.

Reference is first made to FIGS. 1 and 2 in which like parts have been given like index numerals. The instrument of the present invention is generally indicated at 1 and comprises an elongated body 2 having a tubular housing portion 3 and a coaxial cylindrical handle portion 4 of slightly larger diameter.

While the surgical stapling instrument of the present invention can be constructed as a reusable, sterilizable instrument, it lends itself well to manufacture as a single-use, disposable instrument. For purposes of an exemplary showing it will be described in its disposable form wherein its parts are made of metal and plastic suitable for use in a surgical environment and capable of being sterilized by autoclave, ethylene oxide, irradiation or other standard methods.

The body 2 is made up of two mirror image halves molded of plastic material and firmly welded together by means well known in the art. One of the body halves is shown at 2a in FIG. 1, while the other body half is shown at 2b in FIG. 2. Aside from being mirror images of each other, the body halves are otherwise substantially identical.

At its distal end, the tubular housing portion 3 of body 2 mounts a cylindrical staple-containing casing 5 which will be described hereinafter.

An adjustment rod 6 is mounted within the body 2 and extends axially thereof. The distal end of adjustment rod 6 extends beyond casing 5 and has an anvil assembly, generally indicated at 7, affixed thereto. The anvil assembly 7 will be described hereinafter.

At the proximal end of handle portion 4 of body 2 there is rotatively mounted an adjusting knob 8. The adjusting knob 8 is a hollow cylindrical member having a first portion 8a extending beyond the proximal end of handle portion 4. Adjusting knob 8 has a second portion 8b of a lesser outside diameter. The outside diameter of portion 8b is such as to be just nicely received within handle portion 4 and to be rotatable therein. The adjusting knob 8 has a third portion 8c of yet smaller diameter. The portion 8c has a threaded bore 9 extending therethrough.

As indicated above, adjustment knob 8 is rotatively mounted within handle portion 4 of body 1. To maintain the adjusting knob 8 in position within handle portion 4, the body halves 2a and 2b are provided with cooperating, annular, interior flanges. The interior flange of body half 2b is illustrated at 10. It will be understood that the body half 2a has a similar, aligned annular interior flange (not shown). The annular flange 10 of body half 2b and the cooperating annular flange of body half 2a abut a forward shoulder 11 of adjusting knob 8 formed between its portions 8b and 8c. Similarly, a shoulder 12 formed between adjustment knob portions 8a and 8b abuts the proximal end of handle portion 4. Finally, adjusting knob 8 is provided with an annular notch 13, while the interior of handle portion 4 is provided with a matching notch 14. A washer 15 is located in notches 13 and 14 to preclude axial shifting of adjusting knob 8.

While not required, for reasons which will become apparent hereinafter, the adjusting knob 8 is preferably molded of clear plastic. Mounted on its exterior adjacent the proximal end of handle portion 4 there is a ring scale 16. The handle portion 4, adjacent ring scale 16 has a index mark 17 formed thereon. The purpose of ring scale 16 and index mark 17 will be described hereinafter.

The rearward or proximal end of adjusting rod 6 is threaded as at 18. The threaded portion 18 of adjusting rod 6 is engaged in the threaded bore 9 of adjusting knob 8. Each body half 2a and 2b has formed on its interior surface an elongated channel or slot. The channel or slot in body half 2b is shown in broken lines at 19. The identical slot formed on body half 2a is not shown, but when the body halves are joined together, the slot 19 and its counterpart on body half 2a will be diametrically opposed. Adjusting rod 6 has a transverse perforation 20 formed therein. A pin 21 extends through the transverse perforation and the free ends of the pin 21 are slidably engaged in the slot 19 of body half 2b and the similar slot of body half 2a. As a result, pin 21 precludes rotation of adjusting rod 6. It will be evident, however, that as adjusting knob 8 is rotated in one direction, its threaded engagement with adjusting rod 6 will cause the adjusting rod to shift axially of body 1. This, in turn, will cause anvil assembly 7 to shift away from staple-containing casing 5. Rotation of adjusting knob 8 in the opposite direction will cause axial shifting of adjusting rod 6 in the opposite direction with the result that anvil assembly 7 will shift toward staple-containing casing 5.

A cylindrical, hollow driver tube 22 is slidably and coaxially mounted on adjusting rod 6. Driver tube 22 mounts at its distal end a staple driver and a scalpel to be described hereinafter. Near its proximal end the driver tube has an annular array of inwardly extending dimples, one of which is shown at 23. In similar fashion, the driver tube 22 is provided with an annular array of dimples near its distal end, one of which is shown at 24. The driver tube 22 is axially shiftable with respect to the instrument body 1 and the adjusting rod 6, and the arrays of dimples 23 and 24 provide low friction guide means for the driver tube 22 with respect to the adjusting rod 6.

Affixed to the proximal end of driver tube 22 there is a cylindrical spool 25 having annular flanges 25a and 25b at its ends. Body halves 2a and 2b have downwardly depending extensions 26 (see FIG. 1) and 27 (see FIG. 2), respectively. A lever 28 is pivotally mounted on a pin 29, the ends of which are mounted in extensions 26 and 27. The upper portion of lever 28 is bifurcated and terminates in a pair of lobes, one of which is shown in FIG. 2 at 30. The lobes are adapted to lie to either side of spool 25 between the annular spool flanges 25a and 25b. As a result, when lever 28 is squeezed toward handle portion 4 of body 2, the lobes thereof, cooperating with spool 25, will cause the driver tube 22 to shift axially and forwardly of adjusting rod 26.

At the proximal end of the tubular housing portion 3 of body 2 the body halves 2a and 2b are provided with mating internal annular flanges. The internal annular flange of body half 2b is shown at 31 in FIG. 2. The matching annular flange of body half 2a is not shown. The driver tube 22 carries a pair of loosely mounted washers 32 and 33. These washer serve as abutments for the ends of a compression spring 34 mounted on driver tube 22. Washer 32 normally lies in abutment with flange 31 and its counterpart on body half 2a while washer 33 normally abuts the flange 25a of spool 25. In this manner, compression spring 34 serves as a return spring biasing driver tube 22 and lever 28 to their normal unactuated positions as illustrated in FIGS. 1 and 2.

The instrument 1 is provided with a slide safety lockout 35 to prevent inadvertent actuation of lever 28 and driver tube 22. To this end, body half 2b is provided with a slot 36 just behind the downwardly depending extension 27. The body half 2a is provided with a matching slot (not shown). The slide safety lockout 35 is captively and slidably mounted in the slot. The slide safety lockout 35 has a shoulder 37 which engages body half 2b above slot 36. Slide safety lockout 35 will have a similar shoulder (not shown) on it other side to similarly engage body half 2a.

At its rearward end, the slide safety lockout 35 has a portion 38 engagable by the thumb or finger of the surgeon to shift the lockout 35 into and out of its lockout position. At its forward end, the slide safety lockout 35 has a nose portion 39 adapted to engage shoulders formed on the bifurcated portion of lever 28 to prevent actuation of the lever. One such shoulder is shown at 40 in FIG. 2. In FIG. 2 the slide safety lockout 35 is shown in its lockout position preventing actuation of lever 28. It will be apparent from FIG. 2 that the slide safety lockout 35 can be shifted rearwardly so that its nose 39 no longer engages the lever shoulders (one of which is shown at 40) so that the lever is free to be actuated.

Figures 3, 4, 5:
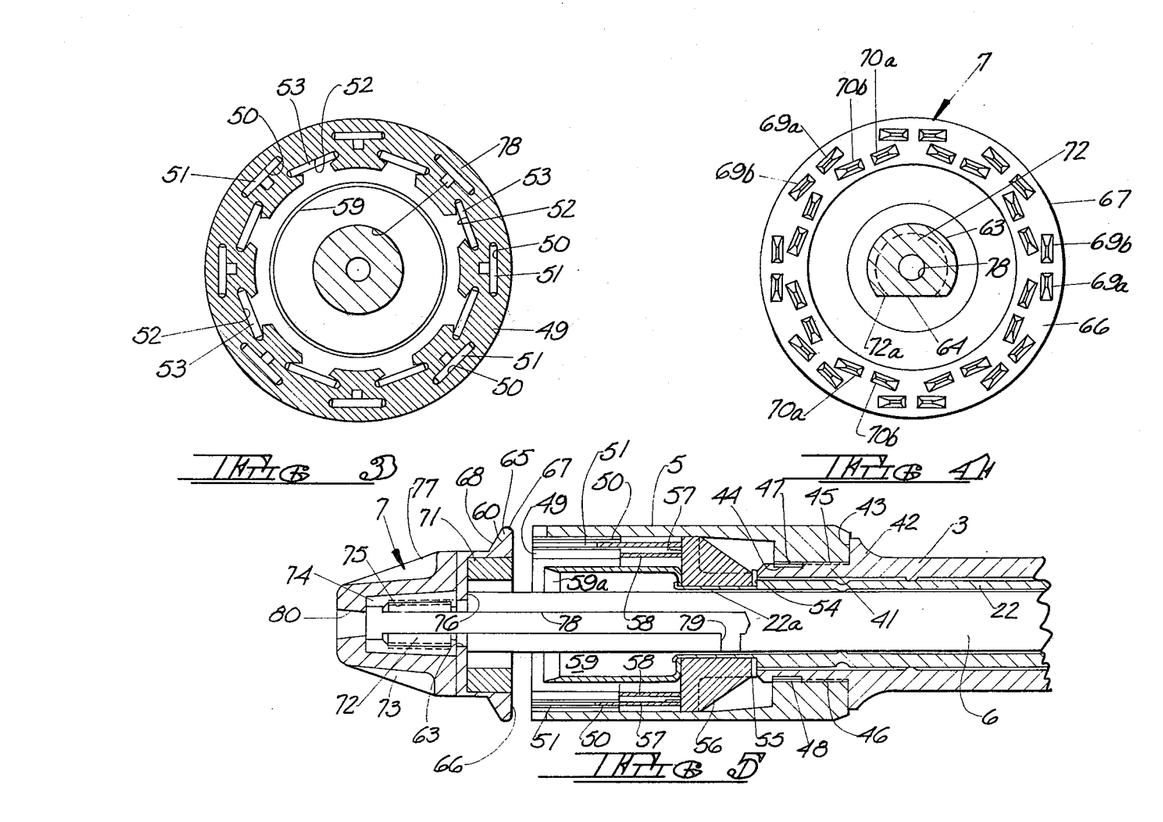
FIG. 3 is an end elevational view of the forward end of the staple-containing casing.
FIG. 4 is an end elevational view of the anvil and anvil nut assembly, viewed from that end which faces the staple-containing casing.
FIG. 5 is an enlarged, fragmentary, longitudinal cross sectional view of the distal end of the instrument illustrating the staple-containing casing and the anvil assembly.

Reference is now made to FIGS. 2, 3 and 5 wherein like parts have been given like index numerals. The forwardmost end 41 of tubular housing portion 3 of body 1 is of reduced diameter. The tubular body portion 3 has an annular flange 42 formed adjacent reduced diameter portion 41 so as to define a shoulder 43.

The cylindrical casing 5 comprises a hollow member and has at its rearward end an axial bore 44 adapted to just nicely receive the reduced diameter portion 41 of tubular housing portion 3 with the rearward end of casing 5 in abutment against shoulder 43. In addition, to assure that casing 5 is in the correct rotative position (so that the staples located therein are in proper alignment with the anvil pockets on the anvil assembly 7) the reduced diameter portion 41 of tubular housing portion 3 may be provided with a plurality of evenly spaced keys (two of which are shown at 45 and 46 while the bore 44 of casing 5 is provided with matching keyways, two of which are shown at 47 and 48. Casing 5 may be molded of plastic material and glued or welded to reduced diameter portion 41 and to flange 42.

Permanently affixed (by gluing, welding or the like) to the inside surface of staple-containing casing 5 there is a staple guide 49. Staple guide 49 may be molded of plaastic material.

As is evident from FIG. 3, the staple guide 49 has a first annular array of channels 50, each containing a staple 51 and a second annular array of channels 52, each containing a staple 53. The second annular array of channels 52 is located within the first annular array of channels 50 and is staggered with respect thereto. Therefore, the instrument is capable of implanting a double staggered row of staples in concentric pattern.

The forwardmost end of driver tube 22 has a reduced portion 22a forming a shoulder 54. Mounted on the reduced portion 22a there is a washer 55 and an annular staple driver 56. Staple driver 56 has a first annular array of tines 57 each of which is aligned with and extends into one of the channels 50 of staple guide 49. Similarly, staple driver 56 has a second annular array of tines 58, each of which extends into one of the channels 52 of staple guide 49. It will be evident that when the driver tube 22 is shifted forwardly by lever 28, the tines 57 and 58 of driver 56 will drive staples 51 and 53 from their respective channels 50 and 52, through the tissue being joined and against anvil assembly 7 to be described hereinafter. A cylindrical scalpel 59 is also mounted on the smaller diameter portion 22a of driver tube 22. The forwardmost end of the portion 22a is upset, thereby captively mounting washer 55, staple driver 56 and scalpel 59 thereon. The forwardmost annular edge of scalpel 59 has an inside bevel 59a formed thereon to provide a cutting edge. Washer 55 assures that the driver 22 imparts uniform force to staple driver 56 and cylindrical scalpel 59. Furthermore, abutment of washer 55 against the end of forwardmost portion 41 of body 2 determines the normal unactuated positions of driver tube 22 and lever 28.

Reference is now made to FIGS. 4 and 5 wherein the anvil assembly 7 is most clearly shown. The anvil assembly comprises an anvil 60, and an anvil nut 73. The anvil 60 is a cylindrical member, the rearward end of which is open and the forward end of which is closed except for an axial perforation 63 therethrough. As is most clearly seen in FIG. 4, perforation 63 is circular in peripheral configuration except for a flat 64, the purpose of which will be described hereinafter. The rearward end of anvil 60 is provided with a thin annular flange 65 which presents a flat annular surface 66 facing toward staple-containing casing 5. The outer peripheral edge of flange 65 is rounded as at 67 and the forward surface 68 of flange 65 slopes forwardly and inwardly. As a result, the anvil 60 has a button-like cross section, the importance of which will be evident hereinafter.

The rearward flat surface 66 of anvil flange 65 is provided with a first annular array of pairs of anvil pockets 69a–69b, each pair of pockets adapted to cooperating with the legs of one of the staples 51. In similar fashion, anvil surface 66 is provided with a second annular array of pairs of anvil pockets 70a–70b, each pair of pockets 70a–70b being adapted to cooperate with the legs of one of the staples 53. As the driver 56 and its tines 57 and 58 drive staples 51 and 53 from channels 50 and 52, through the tissue to be joined and against anvil 60, the pocket pairs 69a–69b and 70a–70b will cause the legs of staples 51 and 53 to be properly crimped, as will be further described hereinafter. A semi-rigid washer 71 is located within anvil 60 to serve as a back-up structure for cylindrical scalpel 59.

The forwardmost end 72 of adjusting rod 6 is of reduced diameter and is externally threaded. The threaded portion 72 has a flat 72a formed thereon which corresponds to the flat 64 of anvil perforation 63. Thus, when anvil 60 is mounted on portion 72 of adjusting rod 6, cooperation of flats 64 and 72a will assure that anvil pockets 69a–69b and 70a–70b will be properly aligned with the staple containing channels 50 and 52 of staple guide 49. This is true since keys 45 and 46 and keyways 47 and 48 determine the rotative position of staple-containing casing 5 and thus staple guide 49 affixed thereto and pin 21 precludes rotation of adjusting rod 6.

Anvil 60 is removably affixed to the threaded portion 72 of adjusting rod 6 by an anvil nut 73. Anvil nut 73 may be molded of plastic or the like and is provided with an axial metallic insert 74. Metallic insert 74 has an axial bore 75 which is internally threaded so as to be engageable on threaded portion 72 of adjusting rod 6. When anvil nut 73 is in place, the anvil 60 will be in abutment with a shoulder 76 on adjusting rod 6 formed by the smaller diameter threaded portion 72.

Anvil nut 73 is preferably frusto-conical in configuration to assist in insertion thereof into the tubular body members to be joined. The exterior surface of anvil nut 73 may be provided with a plurality of longitudinally extending grooves or flutes 77 to render it more easily graspable by the surgeon. This will render the anvil nut 73 and anvil 60 more readily removable during certain surgical procedures such as end-to-side and side-to-end anastomosis, as is well known in the art.

The forward end of adjusting rod 6 is provided with an axial bore 78 leading to a lateral or transverse bore 79. The bore 75 in metallic insert 74 of anvil nut 73 extends completely through the metallic insert and is coaxial with bore 78. In similar fashion, the forwardmost end of the plastic portion of anvil nut 73 has bore 80 formed therein, coaxial with and communicating with bore 75 of metallic insert 74 and bores 78 and 79 of adjusting rod 6. This series of bores constitutes a vent passage, the purpose of which will be described hereinafter.

To complete the structure, the rearwardmost portion 81 of the proximal end of adjusting rod 6 is unthreaded and mounts a cap-like indicator 82. Indicator 82 gives both a tactile and visual indication that the space between anvil 60 and staple-containing casing 5 is within the working or operating gap of the instrument, as will be apparent hereinafter.

The instrument of the present invention having been described, its use and operation may be set forth as follows. For purposes of an exemplary description, the operation of the instrument will be set forth with respect to a simple end-to-end anastomosis procedure and reference is made to FIGS. 2, 5 and 6. At the outset, the anvil 60 is preferably so located that its flat annular surface 66 is in abutment or near abutment with staple-containing casing 5 and staple guide 49. Furthermore, the slide safety lockout 35 should be in its lockout position to prevent inadvertent actuation of lever 28.

Figures 6, 7, 8, 9, 10:
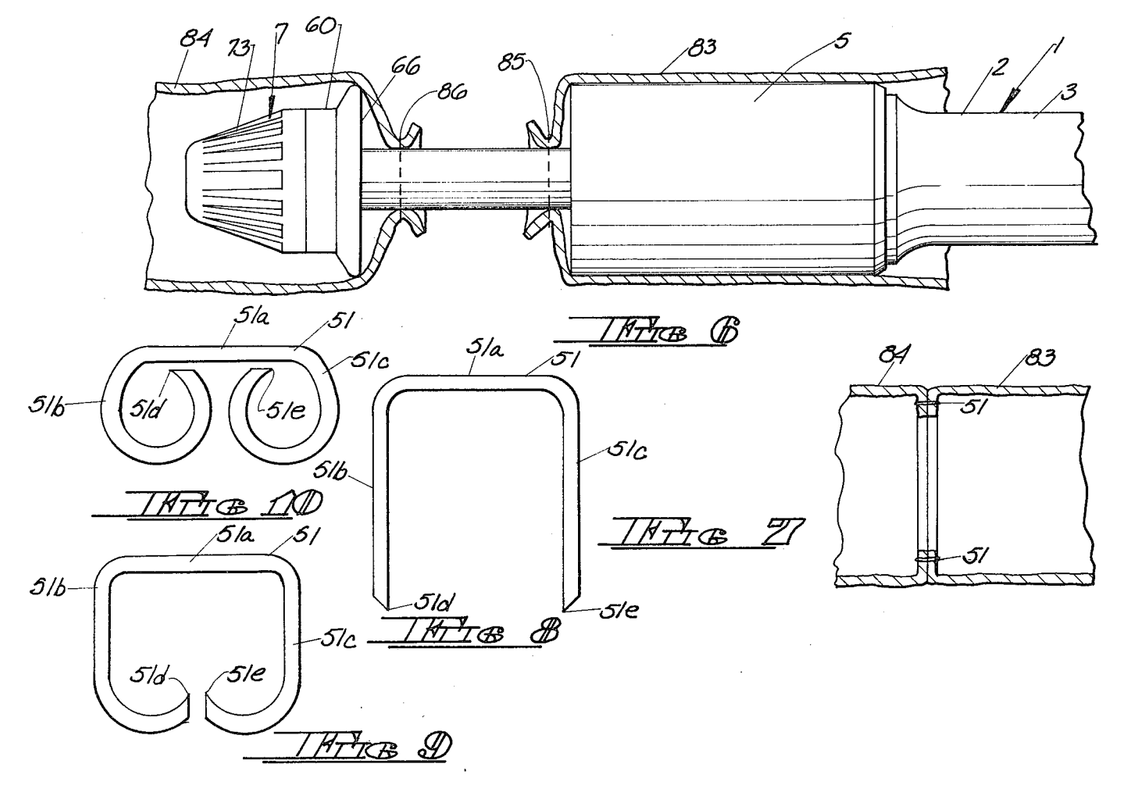
FIG. 6 is a fragmentary view illustrating the arrangement of organs on the instrument prior to placing an end-to-end anastomosis.
FIG. 7 is a fragmentary cross sectional view of the completed end-to-end anastomosis of FIG. 6.
FIG. 8 is an elevational view of a surgical staple for use with the instrument of the present invention.
FIG. 9 is an elevational view of a staple of the instrument of the present invention formed at its maximum height.
FIG. 10 is an elevational view of a surgical staple of the instrument of the present invention formed at its minimum height.

In FIG. 6 two tubular body organs or lumens 83 and 84 to be joined are illustrated. At the time of the end-to-end anastomosis procedure, the distal end of the instrument is inserted into lumen 83 either through a natural opening in the patient's body, if possible, or through an incision made in the side of lumen 83 remote from the anastomotic site. When casing 5 reaches the position shown with respect to lumen 83 in FIG. 6, the adjusting knob 8 is rotated by the surgeon to cause anvil 60 to shift away from casing 5. The end of lumen 83 is then tied about the exposed portion of adjusting rod 6 by means of a simple purse string suture 85, as is shown in FIG. 6. Thereafter, anvil assembly 7 is inserted in lumen 84 and lumen 84 is tied about the exposed portion of adjusting rod 6 by a purse string suture 86, as shown Once the lumens 83 and 84 have been tied to the instrument in the manner shown in FIG. 6, the next step is to set the proper gap between casing 5 and surface 66 of anvil 60 in order to join the lumens by means of the surgical staples. Prior to the anastomotic procedure, the surgeon will have measured the thickness of the tissue of lumens 83 and 84 using a tissue thickness measuring instrument of the type set forth in the above mentioned copending application. The tissue thickness to be joined is, of course, the sum of the tissue thickness of lumen 83 and lumen 84. With this value in mind, the proper gap between staple-containing casing 5 and the surface 66 of anvil 60 can be set by the surgeon in the following manner. First of all, adjusting knob 8 is rotated in a direction to cause surface 66 of anvil 60 to approach the distal end of casing 5. Rotation of adjusting knob 8 is continued until the rearward end of indicator 82 becomes substantially coplanar with the rearward end of adjusting knob 8. This can be ascertained both by feel and visually. If adjusting knob 8 is made of clear plastic, the surgeon can readily watch the indicator 82 approach this coplanar position.

The length of adjusting rod 6 is such that when the rearward end of indicator 82 is coplanar with the end of adjusting knob 8, the surgeon can be assured that the maximum spacing between casing 5 and the surface 66 of anvil 60 within the operating gap of the instrument has been achieved. At this point, the surgeon utilizes the ring scale 16 and index mark 17 to set the final gap in accordance with the tissue thickness measurement previously made.

Once the final gap has been achieved, the slide safety lockout 35 is shifted to its rearward or non-locking position and the surgeon squeezes lever 28 toward handle portion 4 of instrument body 2. The engagement of the lobes (one of which is shown at 30 in FIG. 2) of lever 28 with spool 25 will cause driver tube 22 to shift forwardly with respect to adjusting rod 6. This, in turn, will cause driver 56 and its tines 57 and 58 to drive staples 51 and 53 from their respective staple guide channels 50 and 52. The staples will pass through the tissue of lumens 83 and 84 and the legs of each staple will thereupon enter their respective anvil pocket pairs 69a-69b and 70a-70b to be clinched. Since the surgeon is working at a gap within the operating gap of the instrument, adequate clinching of the staples is assured. Washer 54 further assures that the clinching force imparted by driver 56 will be uniform with respect to all of the staples 51 and 53.

As will be evident from FIGS. 2 and 5, the cylindrical scalpel 59 is offset rearwardly with respect to staples 51 and 53. As a result, scalpel 59 will not begin to cut through the tissue of lumens 83 and 84 until sufficient clinching of the staples has been accomplished. The purpose of cylindrical scalpel 59 is to excise that portion of the tissue of lumens 83 and 84 which is tied to adjusting rod 6. The inside bevel 59a provides a more parallel cut and also forces the excised tissue into the scalpel Washer 54 also insures that uniform force is applied about the cylindrical cutting edge of scalpel 59.

Semi rigid washer 71, located within anvil 60 acts as a cutting board for cylindrical scalpel 59, supporting the tissue being cut. The washer is located flush with anvil surface 66 so as to minimize stretch or pull on the tissue being cut.

The stapling and cutting steps having been performed, it is now necessary to remove the instrument from the anastomotic site. In order to do this, adjusting knob 8 is turned in such a direction as to cause anvil 60 to move away from casing 5. This shifting of anvil 60 to open the gap would produce a partial vacuum due to the piston affect causing the joined lumens to collapse into the gap. This is prevented by the vent system comprising bores 80, 75, 78 and 79, described above with respect to FIG. 5.

Once the anvil assembly 7 is remote from casing 5, the instrument can be removed. This removal requires that the anvil assembly 7 pass through the hole left in the joined organs by cylindrical scalpel 59. This hole is smaller than the original internal diameters of the two organs. The above noted button-configuration of anvil 60 allows the stapled anastomosis to be slipped over a portion of flange 65 while the remainder of the stapled anastomosis approaches adjusting rod 6. By circling the anastomosed tissue about the button-shaped flange 65, the anvil assembly 7 can be brought through the anastomotic site without undue strain on the tissue or the staple lines. The instrument can thereafter readily be removed from lumen 83 and the anastomotic procedure is complete. The completed anastomosis is illustrated in FIG. 7.

As indicated above, the organs of the human alimentary canal are of varying diameters and wall thicknesses even in the same patient. It is therefore desirable that the instrument of the present invention be made available with staple-containing casings of different external diameters. While not intended to be so limited, it has been found that if the instrument is made available with staple-containing casings having external diameters of 21 mm, 25 mm, 28 mm, and 33 mm, most of the internal diameters of the organs of the human alimentary canal will be covered. The instrument may, of course, be made with staple-containing casings 5 of smaller or larger diameters.

The number of staples in the staple-containing casing is dependent upon the external diameter of the casing. Studies have shown that the staples 51 of the outer annular array and the staples 53 of the inner annular should overlap slightly, as shown in FIG. 3, to insure a hemostatic and leak-free closure. However, if the staples 51 and 53 are placed too close together, the blood supply will be comprised and affect healing. Furthermore, if the staples 51 and 53 are arranged too close together, there is less elasticity left in the stapled anastomosis and this renders the instrument more difficult to remove from the anastomotic site. There is also an optimum margin of tissue that must be left between the inner annular array of staples 53 and the cylindrical scalpel 59 since all living tissue retracts when cut.

It will be understood that the instrument 1 of the present invention can be designed with any appropriate operating gap, depending upon its ultimate use. While not intended to be so limited, it has been found that if the instrument 1 is provided with a operating gap of from 1 to 3 mm, it can be used in conjunction with substantially all of the organs of the human alimentary canal. In an exemplary working embodiment of the instrument 1 designed to have a working gap of 1 to 3 mm, the ring scale 16 was graduated from 0 to 3 mm in 0.5 mm increments. At the point where the mark indicated as 3 mm on ring scale 16 was aligned with index mark 17 on the instrument handle portion 4, the rear surface of indicator 82 was coplanar with the rear end of adjusting knob 8, indicating that the maximum value of the operating gap had been achieved.

The instrument of the present invention can be used with one size of surgical staple throughout its operating gap. This is made possible by the configuration of the anvil pockets 69a–69b and 70a–70b which tend to form the surgical staples 51 and 53 into "B" shaped configurations. An exemplary surgical staple 51 is illustrated in FIG. 8. As indicated above, staples 51 and 53 of the two annular arrays are identical. In its initial form, staple 51 has an inverted "U" shape with a substantially horizontal crown portion 51a and downwardly depending legs 51b and 51c. The free ends of legs 51b and 51c are cut at a downwardly and inwardly sloping angle so as to form tissue-penetrating points 51d and 51e. As the surgical staple 51 is advance by staple driver 56 through the tissue to be joined and into a pair of anvil pockets 69a and 69b, the legs 51b and 51c will be clinched toward each other in a curved configuration. FIG. 9 illustrates the staple of FIG. 8 in its fully formed position at the maximum value of the working gap of instrument 1. FIG. 10 illustrates the staple of FIG. 8 in its final configuration when formed at the minimum value of the operating gap of instrument 1. In the exemplary embodiment described above wherein the instrument 1 had an operating gap of 1 to 3 mm, it was found that the surgical staples 51 and 53 would perform as indicated in FIGS. 9 and 10 when provided with a leg length of about 5.5 mm, or about 0.216 inches.

Figure 11:
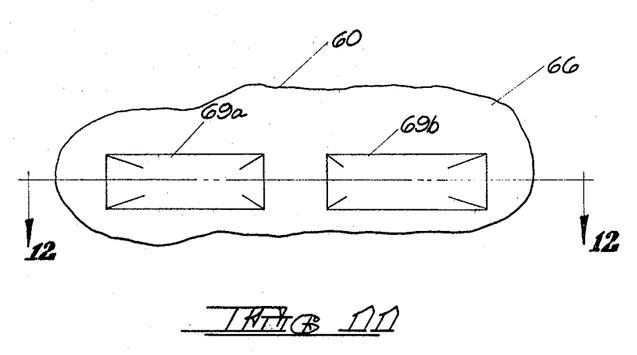
FIG. 11 is a fragmentary plan view of a cooperating pair of anvil pockets in the anvil of the instrument.
Figure 12:
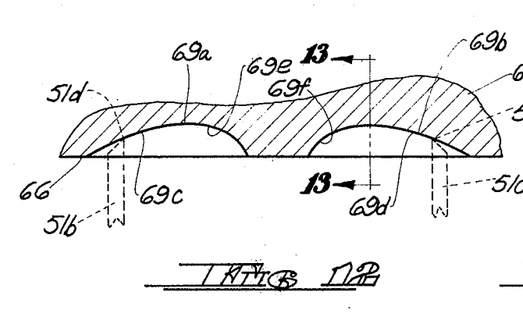
FIG. 12 is a fragmentary cross sectional view taken along section line 12—12 of FIG. 11.
Figure 13:
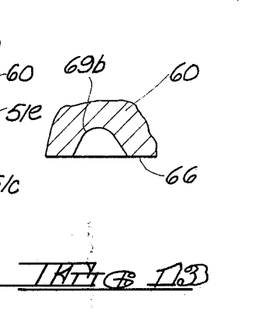
FIG. 13 is a fragmentary cross sectional view taken along section line 13—13 of FIG. 12.

FIGS. 11, 12 and 13 illustrate an exemplary pair of anvil pockets 69a and 69b. It will be understood that all of the pocket pairs 69a–69b are identical and that all of the pocket pairs 70a and 70b are also identical to pocket pairs 69a and 69b.

As is evident from FIGS. 11 through 13 and FIG. 4, the pocket pairs 69a and 69b are formed in the flat rearwardly facing surface 66 of anvil 60. Anvil pocket 69a and anvil pocket 69b are mirror images of each other, and are otherwise identical. Taken together, the anvil pockets 69a and 69b are somewhat longer than the staple crown (i.e., the width of the staple) to enable manufacturing with reasonable tolerance. In FIG. 12, this is shown by virtue of the fact that the legs 51b and 51c of a staple 51 (FIG. 8) are shown in broken lines in their initial positions, just entering pockets 69a and 69b. As will be evident from FIG. 13, the sides of pockets 69a and 69b slope inwardly and downwardly to allow for radial tolerance and to urge the staple legs 51b and 51c toward the center of their respective pockets at the deepest portion thereof.

Turning to FIG. 12, the pockets 69a and 69b have first longitudinally extending large radius portions 69c and 69d, respectively. These large radius portions cooperate with the points 51d and 51e of staple legs 51b and 51c, respectively, to cause them to bend toward each other. Anvil pockets 69a and 69b also have longitudinally extending smaller radius portions 69e and 69f, respectively. As the staple legs 51b and 51c are driven further toward anvil 60, small radius anvil pocket portions 69e and 69f will cause the staple legs 51b and 51c to form a radius of curvature of their own. The gap setting of instrument 1 will determine the ultimate configuration of the staple 51 between that shown in FIG. 9 and that shown in FIG. 10, as described above. At all gap settings within the working gap of the instrument, the staple 51 will be formed into a B-shaped configuration.

To enable the instrument 1 of the present invention to utilize surgical staples of a single leg length throughout the working gap of the instrument, the essential elements include the leg length, wire diameter and tensile strength of the surgical staple 51 and the contour of anvil pockets 69a and 69b. In an exemplary working embodiment, the staple 51 was made of stainless steel having a wire diameter of about 0.011 inch, a tensile strength of from about 150,000 to about 160,000 psi and a leg length of about 0.216 inch. Anvil pockets 69a and 69b had an overall length, including the space therebetween, of about 0.182 inch, each of pockets 69a and 69b having a maximum width of about 0.028 inch and a maximum depth of about 0.015 inch. The large radius portions 69c and 69d had a radius of about 0.081 inch. The smaller radius portions 69e and 69f each had a radius of about 0.035 inch. In this working embodiment, staples 51 were successfully and reliably formed into acceptable B-shapes throughout a working gap of from 1 to 3 mm.

Modifications may be made in the invention without departing from the spirit of it. For example, ring scale 16 could be mounted on the end of instrument body 2 adjacent adjustment knob 8 and adjustment knob 8 could carry indicator mark 17.

What is claimed is:

1. A surgical stapling instrument of the type used to join together tubular body organs, said surgical stapling instrument comprising an elongated body having first and second ends, a cylindrical casing affixed coaxially on said first end of said body, at least one annular array of surgical staples mounted within said casing, an adjusting rod coaxially mounted within said body and said casing, said adjusting rod having a first end extending beyond said casing, an anvil mounted on said first end of said adjusting rod, said anvil having an anvil surface facing said casing, an adjustment knob mounted at said second end of said body, said adjustment knob being hollow, said adjusting rod being operatively connected to said adjustment knob, said adjusting rod and said anvil being axially shiftable by operation of said adjustment knob between a position wherein said anvil surface is adjacent said casing and a position wherein said anvil surface is spaced from said casing, a staple driver and a cylindrical scalpel located within said casing, means to shift said staple driver and said scalpel from a retracted position within said casing toward said anvil to drive said staples through said tubular body organs to be joined, to clinch said staples against said anvil surface and to sever excess portions of said tubular body organs over a range of distances between said anvil surface and said casing constituting a working gap of said instrument, said adjusting rod having a second end located within said hollow adjustment knob, indicator means mounted on said second end of said adjusting rod and being so configured as to give both visual and tactile indications that the distance between said anvil surface and said casing is at and within said working gap, a scale in association with one of said adjustment knob and said second end of said body and a cooperating indicator mark on the other of said adjustment knob and said second end of said body enabling final adjustment of said distance between said anvil surface and said casing within said working gap according to the thickness of the tissue of the tubular body organs being joined.

2. The structure claimed in claim 1 wherein said means to shift said driver and scalpel comprises a hollow driver tube slidably mounted on said adjusting rod and having first and second ends, said scalpel and said driver being mounted at said first end of said driver tube, a lever pivotally affixed to said instrument body, said lever being operatively connected to said second end of said hollow driver tube, said lever being pivotable and said driver tube being shiftable thereby from a normal position wherein said scalpel and driver are in their retracted positions to an actuated position wherein said scalpel and said driver are shifted toward said anvil, and resilient means biasing said lever and said driver tube to said normal position.

3. The structure claimed in claim 2 including releasable lockout means to lock said lever in its normal position.

4. The structure claimed in claim 2 wherein said hollow adjustment knob has an annular rearward end, said indicator means on said second end of said adjusting rod has a rearward surface so located as to be flush with the rearward end of said adjustment knob when said distance between said anvil surface and said casing is at the maximum of said working gap and as to extend rearwardly beyond said rearward end of said adjustment knob when said distance between said anvil surface and said casing is within said working gap.

5. The structure claimed in claim 4 wherein said anvil is of button-like configuration comprising a body portion of lesser transverse dimension than the diameter of said staple containing casing, near one end said body portion flaring outwardly to form a thin annular flange having a maximum diameter substantially the same as the diameter of said casing, said end of said anvil having said flange comprising said anvil surface.

6. The structure claimed in claim 5 wherein said anvil surface has at least one annular array of pairs of anvil pockets formed therein, the number of anvil pocket pairs being equal to the number of said surgical staples mounted in said casing, each of said surgical staples comprising a U-shaped element having a pair of legs joined by a crown portion, the anvil pockets of each pair being mirror images of each other and being spaced from each other so as to each receive one of the legs of the same surgical staple, the pockets of a pair both comprising elongated depressions each having a first longitudinal curved large radius bottom surface portion to be first contacted by their respective staple legs to bend said legs toward each other and a second longitudinal curved bottom surface portion of lesser radius to cause said legs to form into oppositely directed curves so that said staple achieves a B-shaped configuration whereby staples of a single leg length will be adequately clinched at any gap setting within said working gap.

7. The structure claimed in claim 6 including said first and second concentric annular arrays of surgical staples in said casing, said annular arrays of surgical staples being circumferentially offset with respect to each other, said anvil having first and second concentric annular arrays of pairs of anvil pockets, said annular arrays of anvil pocket pairs being circumferentially offset with respect to each other such that each anvil pocket pair is aligned with one of said surgical staples in said casing.

8. The structure claimed in claim 7 including an axial bore in said adjusting rod extending from said first end of said adjusting rod and terminating in a transverse bore forming an opening in the side of said adjusting rod, said axial bore being of such length that when said tubular body organs are joined by said surgical staples said axial and said transverse bores comprise a vent passage to equalize the pressure on either side of said joinder of said tubular body organs.

9. The structure claimed in claim 8 including releasable lockout means to lock said lever in its normal position.

10. The structure claimed in claim 9 wherein said adjustment knob is transparent, said adjusting rod indicator being visible therethrough.

11. The structure claimed in claim 1 including first and second concentric annular arrays of surgical staples in said casing, said arrays being circumferentially offset with respect to each other.

12. The structure claimed in claim 1 wherein said hollow adjustment knob has an annular rearward end, said indicator means on said second end of said adjusting rod has a rearward surface so located as to be flush with the rearward end of said adjustment knob when said distance between said anvil surface and said casing is at the maximum of said working gap and as to extend rearwardly beyond said rearward end of said adjustment knob when said distance between said anvil surface and said casing is within said working gap.

13. The structure claimed in claim 12 wherein said adjustment knob is transparent, said adjusting rod indicator being visible therethrough.

14. The structure claimed in claim 1 wherein said anvil is removably affixed to said first end of said adjustment rod.

15. The structure claimed in claim 1 wherein said anvil is of button-like configuration comprising a body portion of lesser transverse dimension than the diameter of said staple containing casing, near one end said body portion flares outwardly to form a thin annular flange having a maximum diameter substantially the same as the diameter of said casing, said end of said anvil having said flange comprising said anvil surface.

16. The structure claimed in claim 15 wherein said anvil end having said flange has a central depression formed therein, a washer-like member of semi-rigid material being mounted in said depression and comprising backing means for said cylindrical scalpel.

17. The structure claimed in claim 15 wherein said anvil surface has at least one annular array of pairs of anvil pockets formed therein, the number of anvil pocket pairs being equal to the number of said surgical staples mounted in said casing, each of said surgical staples comprising a U-shaped element having a pair of legs joined by a crown portion, the anvil pockets of each pair being mirror images of each other and being spaced from each other so as to each receive one of the legs of the same surgical staple, the pockets of a pair both comprising elongated depressions each having a first longitudinal curved large radius bottom surface portion to be first contacted by their respective staple legs to bend said legs toward each other and a second longitudinal curved bottom surface portion of lesser radius to cause said legs to form into oppositely directed curves so that said staple achieves a B-shaped configuration whereby staples of a single leg length will be adequately clinched at any gap setting within said working gap.

18. The structure claimed in claim 1 including an axial bore in said adjusting rod extending from said first end of said adjusting rod and terminating in a transverse bore forming an opening in the side of said adjusting rod, said axial bore being of such length that when said tubular body organs are joined by said surgical staples said axial and said transverse bores comprise a vent passage to equalize the pressure on either side of said joinder of said tubular body organs.

19. The structure claimed in claim 1 wherein said anvil surface has at least one annular array of pairs of anvil pockets formed therein, the number of anvil pocket pairs being equal to the number of said surgical staples mounted in said casing, each of said surgical staples comprising a U-shaped element having a pair of legs joined by a crown portion, the anvil pockets of each pair being mirror images of each other and being spaced from each other so as to each receive one of the legs of the same surgical staple, the pockets of a pair both comprising elongated depressions each having a first longitudinal curved large radius bottom surface portion to be first contacted by their respective staple legs to bend said legs toward each other and a second longitudinal curved bottom surface portion of lesser radius to cause said legs to form into oppositely directed curves so that said staple achieves a B-shaped configuration whereby staples of a single leg length will be adequately clinched at any gap setting within said working gap.

20. The structure claimed in claim 19 including said first and second concentric annular arrays of surgical staples in said casing, said annular arrays of surgical staples being circumferentially offset with respect to each other, said anvil having first and second concentric annular arrays of pairs of anvil pockets, said annular arrays of anvil pocket pairs being circumferentially offset with respect to each other such that each anvil pocket pair is aligned with one of said surgical staples in said casing.

21. An anvil having an anvil surface for use with a surgical stapling instrument of the type employed to join together tubular body organs and of the type having a cylindrical casing containing at least one annular array of surgical staples, means to support and shift said anvil between a position wherein said anvil surface is adjacent said casing and a position wherein said anvil surface is spaced from said casing, a driver for said surgical staples and a cylindrical scalpel located within said casing and means to shift said staple driver and said scalpel from a retracted position within said casing toward said anvil surface to drive said surgical staples through the tubular body organs to be joined to clinch said surgical staples against said anvil surface and to sever excess portions of said tubular body organs over a range of distances between said anvil surface and said casing constituting a working gap of said instrument, said anvil being of button-like configuration and comprising a body portion of lesser transverse dimension than the diameter of said staple containing casing, near one end said body portion flaring outwardly to form a thin annular flange having a maximum diameter substantially the same as the diameter of said casing, said end of said anvil having said flange comprising said anvil surface.

22. The structure claimed in claim 21 wherein said anvil end having said flange has a central depression formed therein, a washer-like member of semi-rigid material being mounted in said depression and comprising backing means for said cylindrical scalpel.

23. An anvil having an anvil surface for use with a surgical stapling instrument of the type employed to join together tubular body organs and of the type having a cylindrical casing containing at least one annular array of surgical staples, means to support and shift said anvil between a position wherein said anvil surface is adjacent said casing and a position wherein said anvil surface is spaced from said casing, a driver for said surgical staples and a cylindrical scalpel located within said casing and means to shift said staple driver and said scalpel from a retracted position within said casing toward said anvil surface to drive said surgical staples through the tubular body organs to be joined, to clinch said surgical staples against said anvil surface and to sever excess portions of said tubular body organs over a range of distances between said anvil surface and said casing constituting a working gap of said instrument, said anvil surface having at least one annular array of pairs of anvil pockets formed therein, the number of anvil pocket pairs being equal to the number of said surgical staples mounted in said casing, each of said surgical staples comprising a U-shaped element having a pair of legs joined by a crown portion, the anvil pockets of each pair being mirror images of each other and being spaced from each other so as to each receive one of the legs of the same surgical staple, the pockets of a pair both comprising elongated depressions each having a first longitudinal curved large radius bottom surface portion to be first contacted by their respective staple legs to bend said legs toward each other and a second longitudinal curved bottom surface portion of lesser radius to cause said legs to form oppositely directed curves so that said staple achieves a B-shaped configuration, whereby staples of a single leg length will be adequately clinched at any distance between said anvil surface and said casing within said working gap.

24. The structure claimed in claim 23 wherein said anvil is of button-like configuration comprising a body portion of lesser transverse dimension than the diameter of said staple containing casing, near one end said body portion flaring outwardly to form a thin annular flange having a maximum diameter substantially the same as the diameter of said casing, said end of said anvil having said flange comprising said anvil surface.

25. The structure claimed in claim 23 including first and second concentric annular arrays of surgical staples in said casing, said annular arrays of surgical staples being circumferentially offset with respect to each other, said anvil having first and second concentric annular arrays of pairs of anvil pockets, said annular arrays of anvil pocket pairs being circumferentially offset with respect to each other such that each anvil pocket pair is aligned with one of said surgical staples in said casing.

26. The structure claimed in claim 24 wherein said anvil end having said flange has a central depression formed therein, a washer-like member of semi-rigid material being mounted in said depression and comprising backing means for said cylindrical scalpel.

27. The structure claimed in claim 24 including first and second concentric annular arrays of surgical staples in said casing, said annular arrays of surgical staples being circumferentially offset with respect to each other, said anvil having first and second concentric annular arrays of pairs of anvil pockets, said annular arrays of anvil pocket pairs being circumferentially offset with respect to each other such that each anvil pocket pair is aligned with one of said surgical staples in said casing.

28. The structure claimed in claim 27 wherein said anvil end having said flange has a central depression formed therein, a washer-like member of semi-rigid material being mounted in said depression and comprising backing means for said cylindrical scalpel.

29. The structure claimed in claim 1 including vent means to equalize the pressure on either side of said joinder of said tubular body organs.

* * * * *

REEXAMINATION CERTIFICATE (471st)

United States Patent [19]

Rothfuss

[11] B1 4,319,576

[45] Certificate Issued  Feb. 25, 1986

[54] INTRALUMENAL ANASTOMOSIS SURGICAL STAPLING INSTRUMENT

[75] Inventor: Robert G. Rothfuss, Bellevue, Ky.

[73] Assignee: Senmed, Inc., Cincinnati, Ohio

Reexamination Request:
No. 90/000,656, Oct. 24, 1984

Reexamination Certificate for:
Patent No.: 4,319,576
Issued: Mar. 16, 1982
Appl. No.: 124,954
Filed: Feb. 16, 1980

[51] Int. Cl.[4] .............. A61B 17/04; A61B 17/32
[52] U.S. Cl. .................. 128/305; 227/19; 128/334 R
[58] Field of Search ............. 128/334, 334 C, 305, 128/335; 227/19, 155, 120, DIG. 1

[56] References Cited

U.S. PATENT DOCUMENTS

| | | | |
|---|---|---|---|
| 2,638,901 | 5/1953 | Sugarbaker | 128/334 |
| 3,388,847 | 6/1968 | Kasulin et al. | 227/19 |

FOREIGN PATENT DOCUMENTS 2822803  12/1978  Fed. Rep. of Germany

OTHER PUBLICATIONS

File wrapper of S. N. 880,965 filed May 26, 1977.

*Primary Examiner*—Stephen C. Pellegrino
*Attorney, Agent, or Firm*—Frost & Jacobs

[57] ABSTRACT

A disposable surgical stapling instrument for the joining together of tubular body organs such as the organs of the alimentary canal. The instrument comprises an elongated body having a tubular housing portion and a coaxial cylindrical handle portion. The tubular housing portion supports at its free end a coaxial cylindrical casing containing at least one annular array of surgical staples. An adjusting rod is coaxially and non-rotatively mounted within the instrument body and has a first end extending beyond the staple-containing casing. An anvil, of improved configuration for easier removal from the anastomotic site, is removably mounted by means of an anvil nut on the first end of the adjusting rod facing the staple-containing casing. By means of an adjustment knob at the free end of the instrument body handle portion, the anvil and the adjusting rod are shiftable axially of the instrument body between a position wherein the anvil is adjacent the staple-containing casing and a position wherein the anvil is spaced from the staple-containing casing. The anvil has a plurality of anvil pockets formed therein to clinch the staples over a range of distances between the anvil and the staple casing constituting a working gap. The adjustment rod has a second end mounting an indicator cooperating with the adjustment knob to give both visual and tactile indications that the anvil is spaced from the staple casing within the operating gap. A ring scale is mounted on the adjusting knob enabling accurate setting of the distance between the anvil and the staple casing, within the working gap, according to the thickness of the tissue of the tubular body organs being joined. The instrument is also provided with a lever actuated staple driver and scalpel assembly and a slide safety lockout to prevent undesired actuation of the lever.

REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 1–20 and 23–29 is confirmed.

Claim 21 is determined to be patentable as amended.

Claim 22 dependent on an amended claim, is determined to be patentable.

New claim 30 is added and determined to be patentable.

21. [An anvil having an anvil surface for use within] *In* a surgical stapling instrument of the type employed to join together tubular body organs and of the type having *an anvil including an anvil surface,* a cylindrical casing containing at least one annular array of surgical staples, means to support and shift said anvil between a position wherein said anvil surface is adjacent said casing and a position wherein said anvil surface is spaced from said casing, a driver for said surgical staples and a cylindrical scalpel located within said casing and means to shift said staple driver and said scalpel from a retracted position within said casing toward said anvil surface to drive said surgical staples through the tubular body organs to be joined to clinch said surgical staples against said anvil surface and to sever excess portions of said tubular body organs over a range of distances between said anvil surface and said casing constituting a working gap of said instrument, *the improvement in combination therewith comprising* a [said anvil being of] button-like configuration [and comprising] *for said anvil including* a body portion of lesser transverse dimension than the diameter of said staple containing casing, near one end of said body portion flaring outwardly to form a thin annular flange having a maximum diameter substantially the same as the diameter of said casing, said end of said anvil having said flange comprising said anvil surface, *said anvil flange being completely exposed whereby the peripheral edge of the flange will initially contact the inner wall of one of the tubular organs, the exposed flange further allowing the stapled portions of the organs to be slipped over and circled about in contact with the flared surface of the flange to facilitate removal of the instrument.*

*30. The structure claimed in claim 21 wherein said forward surface slopes forwardly and inwardly.*

* * * * *